(12) United States Patent
Binder

(10) Patent No.: US 8,636,358 B2
(45) Date of Patent: Jan. 28, 2014

(54) LENS WITH VARIABLE REFRACTION POWER FOR THE HUMAN EYE

(76) Inventor: Helmut Binder, Berlin (DE)

( * ) Notice: Subject to any disclaimer, the term of this patent is extended or adjusted under 35 U.S.C. 154(b) by 0 days.

(21) Appl. No.: 13/318,808

(22) PCT Filed: May 15, 2010

(86) PCT No.: PCT/EP2010/002986
§ 371 (c)(1),
(2), (4) Date: Dec. 6, 2011

(87) PCT Pub. No.: WO2010/133317
PCT Pub. Date: Nov. 25, 2010

(65) Prior Publication Data
US 2012/0092612 A1    Apr. 19, 2012

Related U.S. Application Data

(60) Provisional application No. 61/284,863, filed on Dec. 28, 2009.

(30) Foreign Application Priority Data

May 17, 2009  (DE) .......................... 10 2009 021 699
Sep. 11, 2009  (DE) .......................... 10 2009 040 933

(51) Int. Cl.
*G02C 7/04*    (2006.01)
(52) U.S. Cl.
USPC .................................................. 351/159.03
(58) Field of Classification Search
USPC ........ 351/159.02–159.38; 623/4.1, 6.11, 6.22
See application file for complete search history.

(56) References Cited

U.S. PATENT DOCUMENTS

| | | | |
|---|---|---|---|
| 5,800,530 A * | 9/1998 | Rizzo, III | 623/6.22 |
| 6,619,799 B1 | 9/2003 | Blum et al. | |
| 2004/0117011 A1 * | 6/2004 | Aharoni et al. | 623/6.11 |
| 2005/0099594 A1 | 5/2005 | Blum et al. | |
| 2006/0155372 A1 * | 7/2006 | Coroneo | 623/4.1 |
| 2006/0206205 A1 | 9/2006 | Azar | |
| 2009/0033863 A1 | 2/2009 | Blum et al. | |
| 2009/0105817 A1 | 4/2009 | Bretthauer et al. | |

* cited by examiner

*Primary Examiner* — Darryl J Collins
(74) *Attorney, Agent, or Firm* — Occhiuti & Rohlicek LLP

(57) ABSTRACT

The present invention comprises a lens with variable refraction power as well as an optical system for the use as, preferably accommodating, visual aid. The lens is designed as an intraocular lens or as a contact lens. The general idea of the invention is to determine the accommodation requirement from the position of the eyes relative to one another. This is possible, since the accommodation requirement and the eyes' motor activity are closely related. According to a first embodiment, the present invention claims a lens with variable refraction power, which possesses the following components: means for adaptation of the refraction power, especially by a change of the lens' curvature as a reaction to a control signal; at least one position locator; means for detection of the relative position of the position locator to at least another position locator arranged on another lens; means for generation of the control signal for adaptation of the refraction power of the lens to the detected relative position and at least one device for power supply for at least parts of the components of the lens.

20 Claims, 10 Drawing Sheets

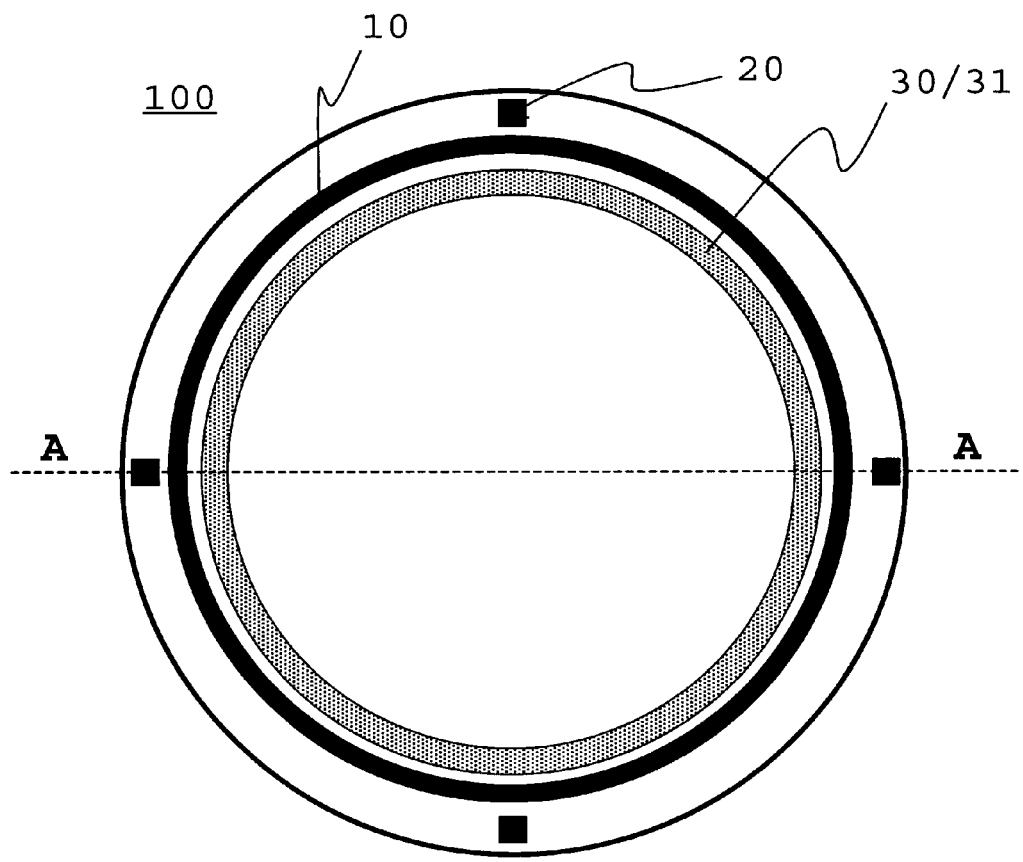
Fig. 1.a
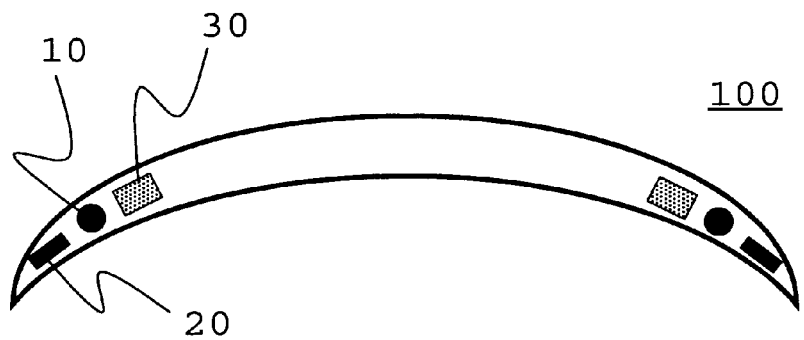
Fig. 1.b

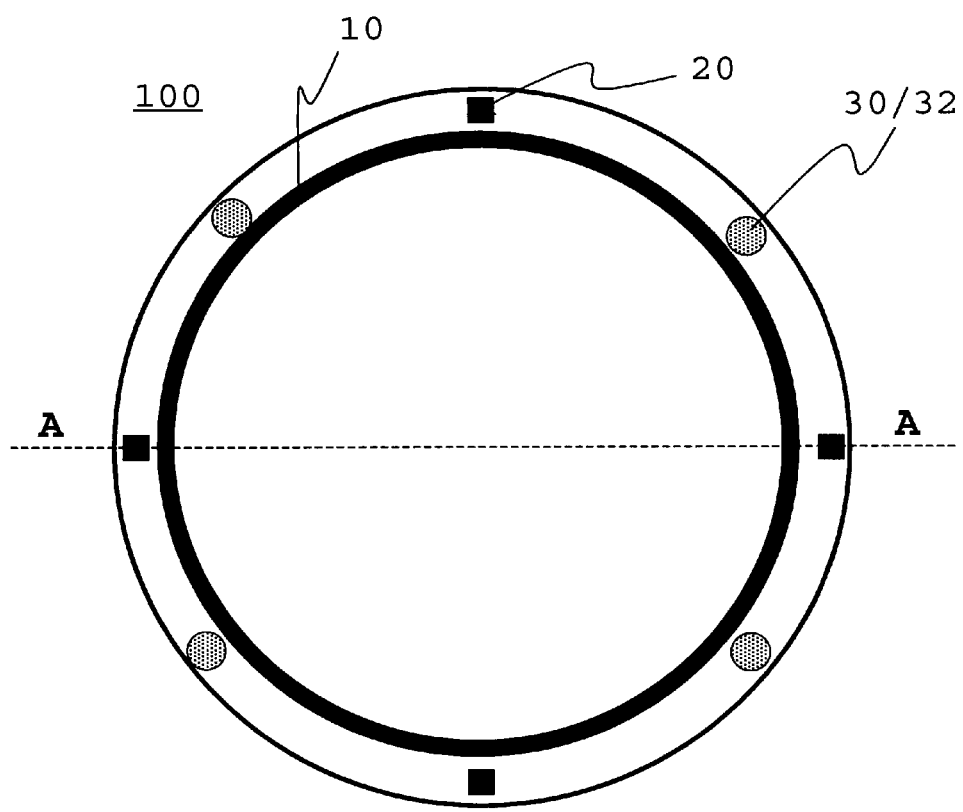
Fig. 2.a
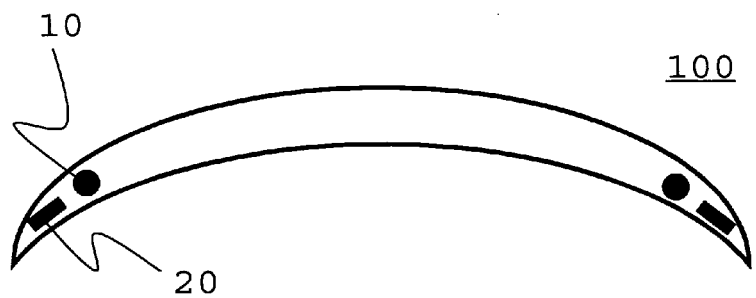
Fig. 2.b

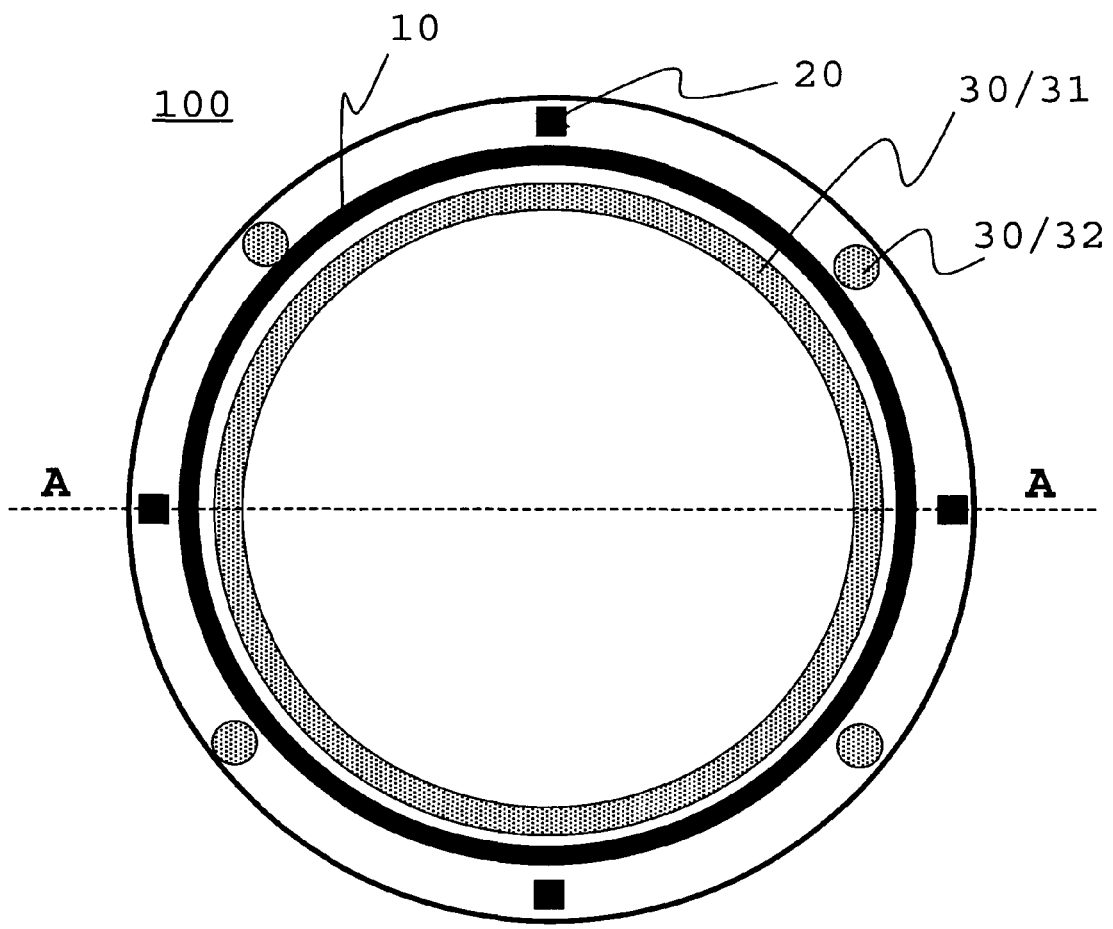
Fig. 3.a
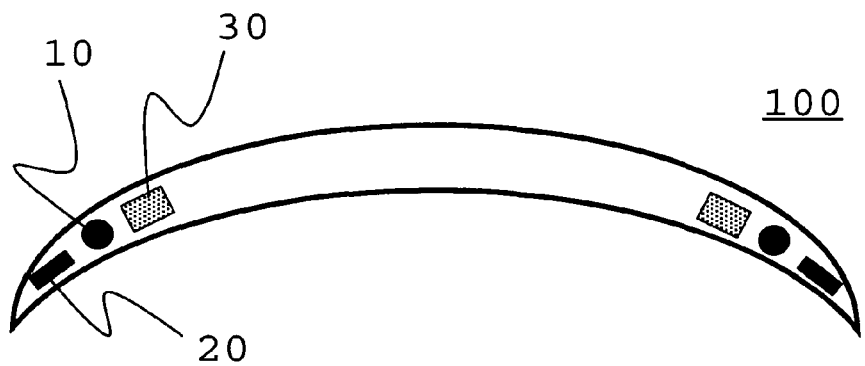
Fig. 3.b

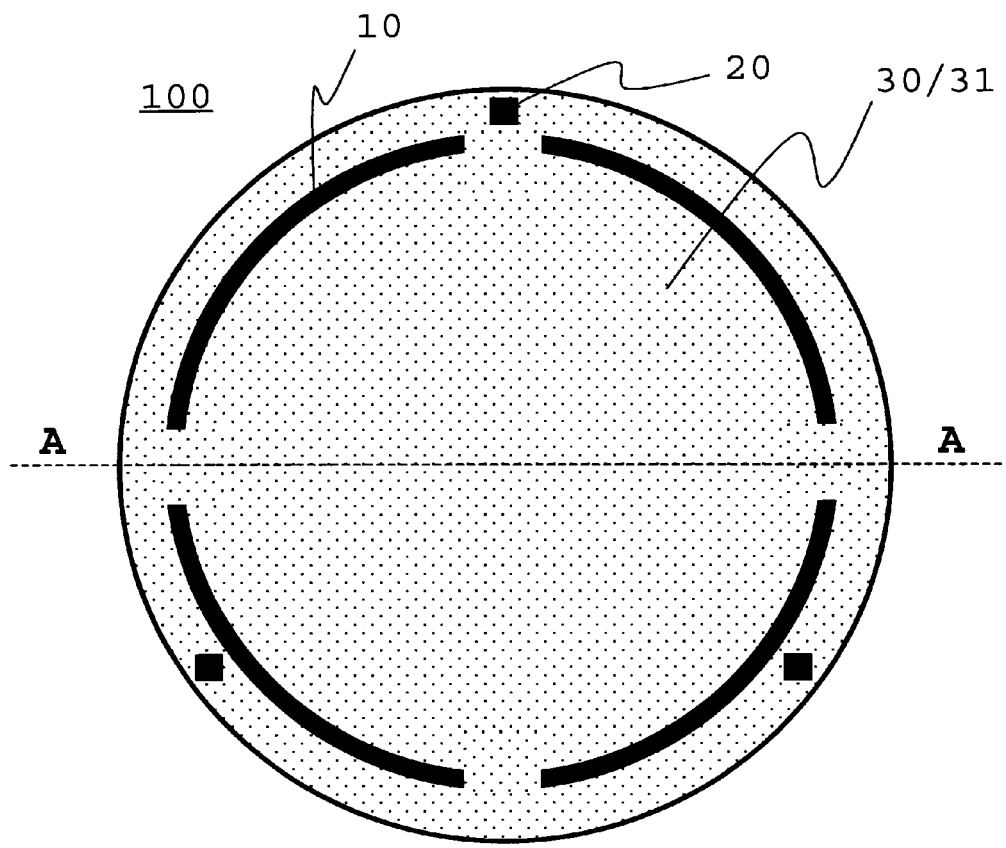
Fig. 4.a
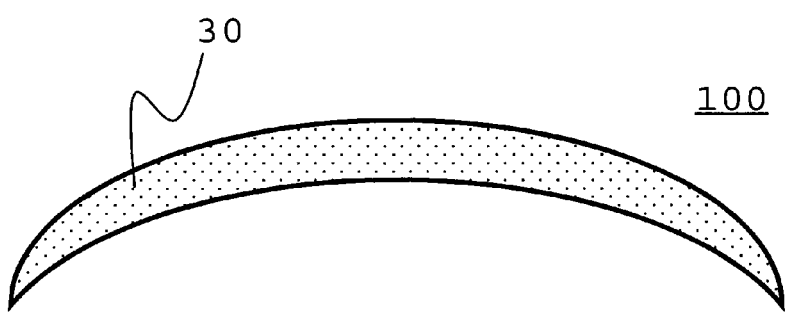
Fig. 4.b

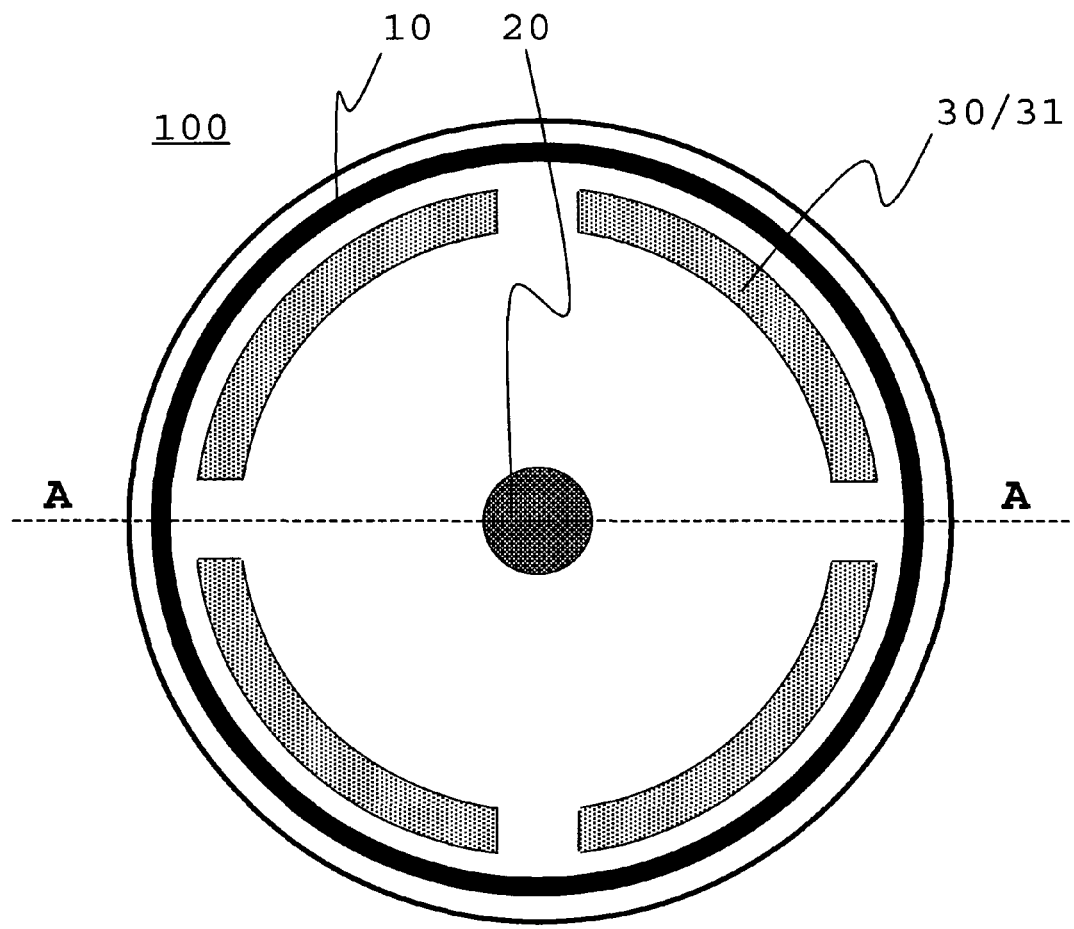
Fig. 5.a
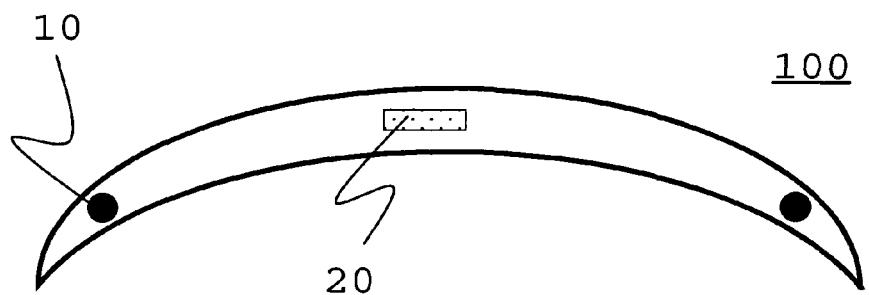
Fig. 5.b

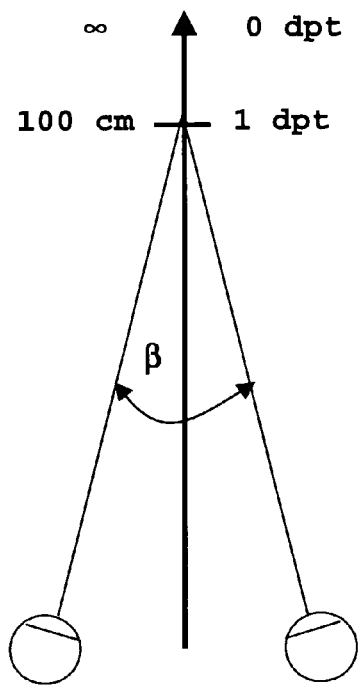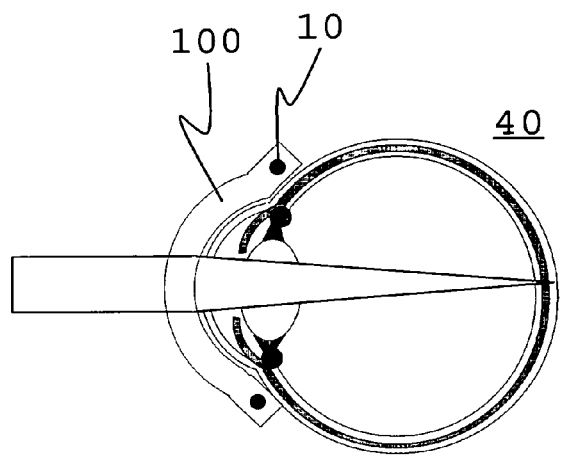
Fig. 6.a
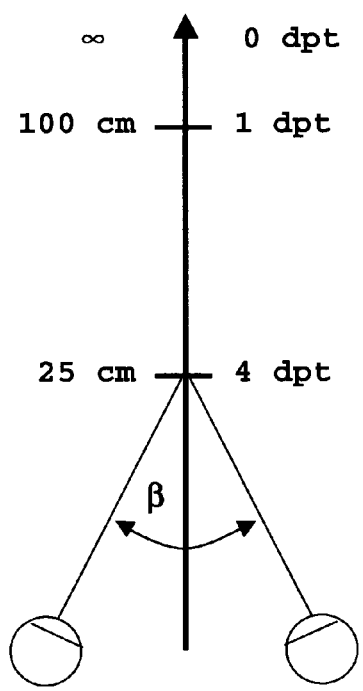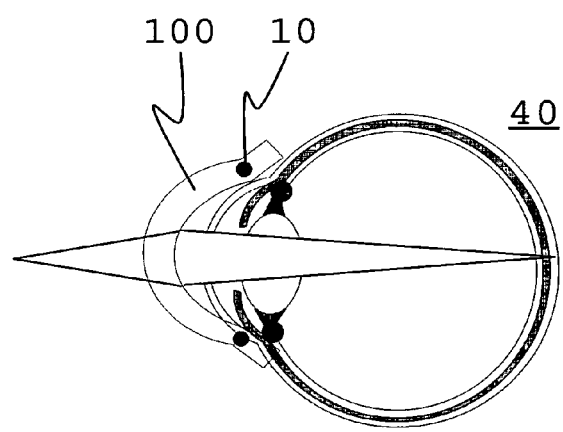
Fig. 6.b

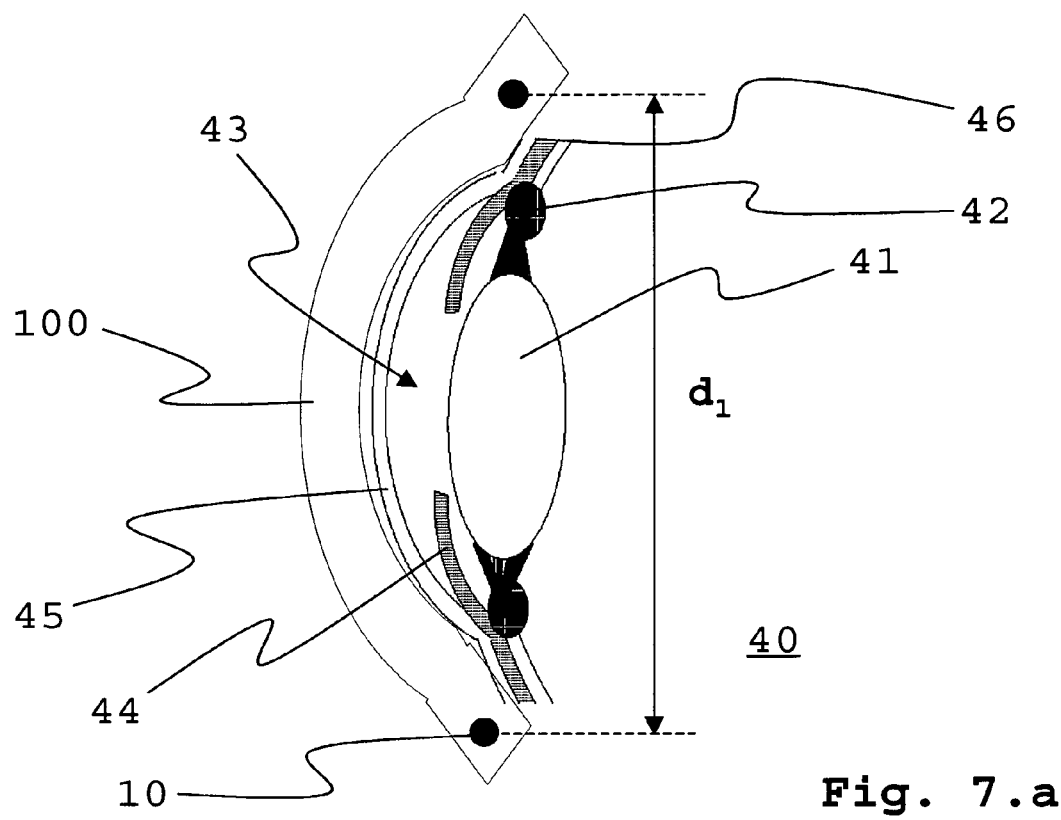
Fig. 7.a
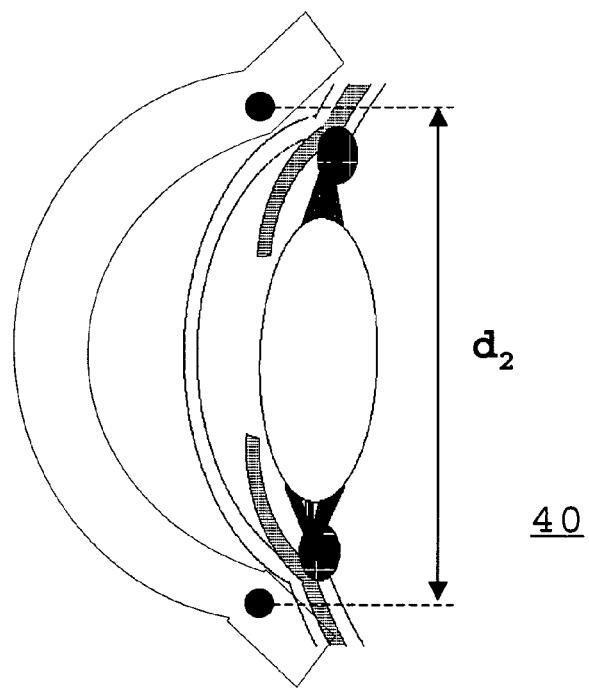
Fig. 7.b

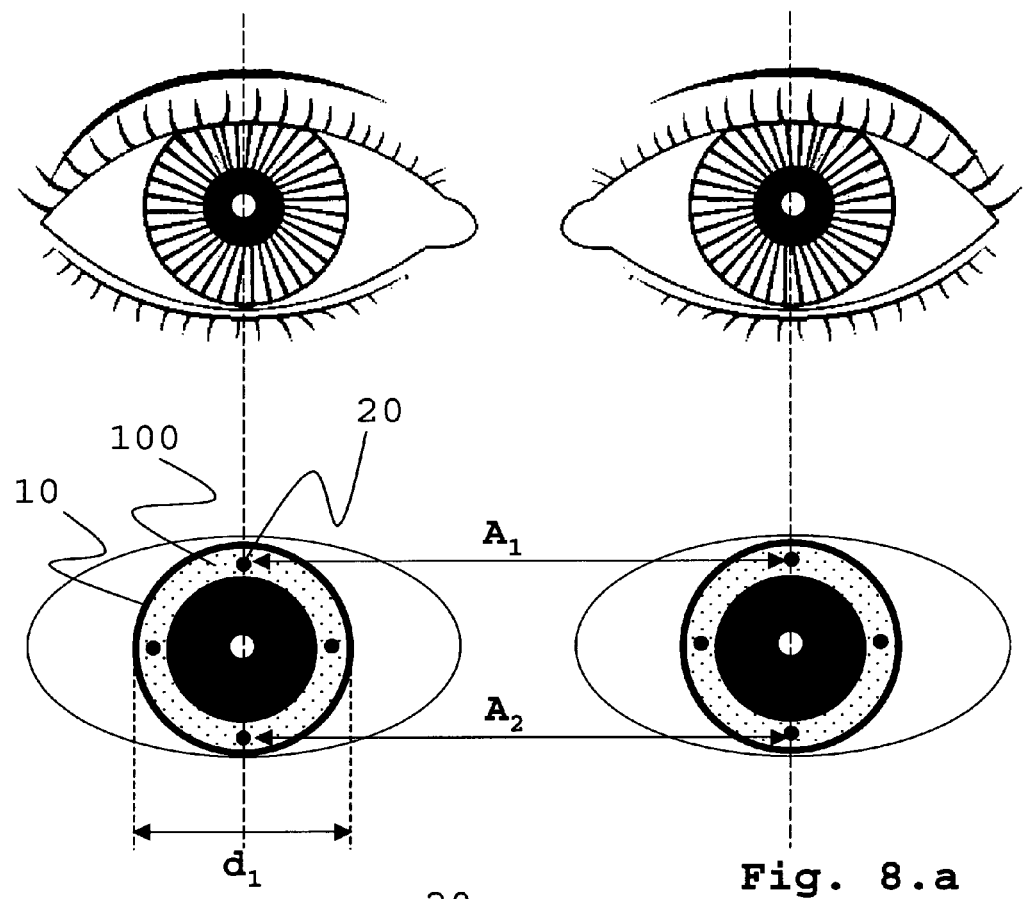
Fig. 8.a
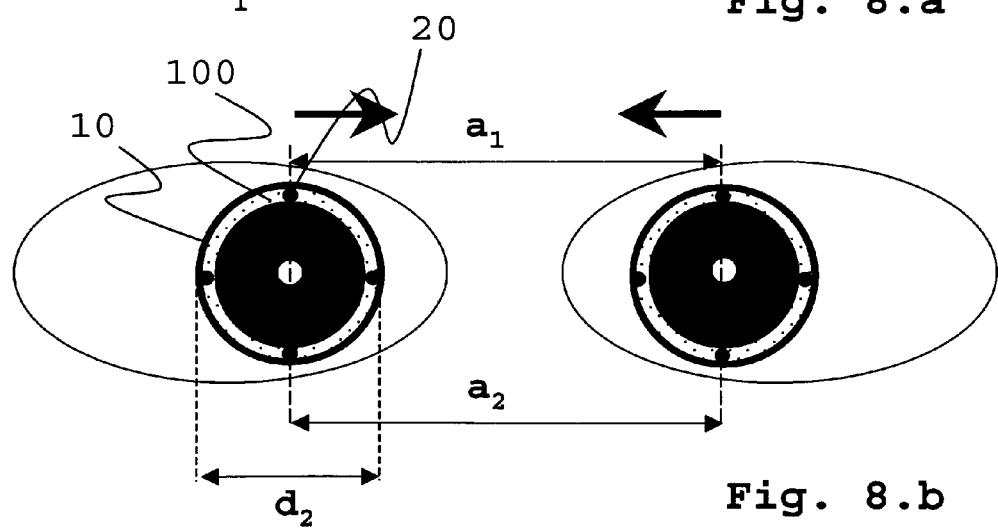
Fig. 8.b

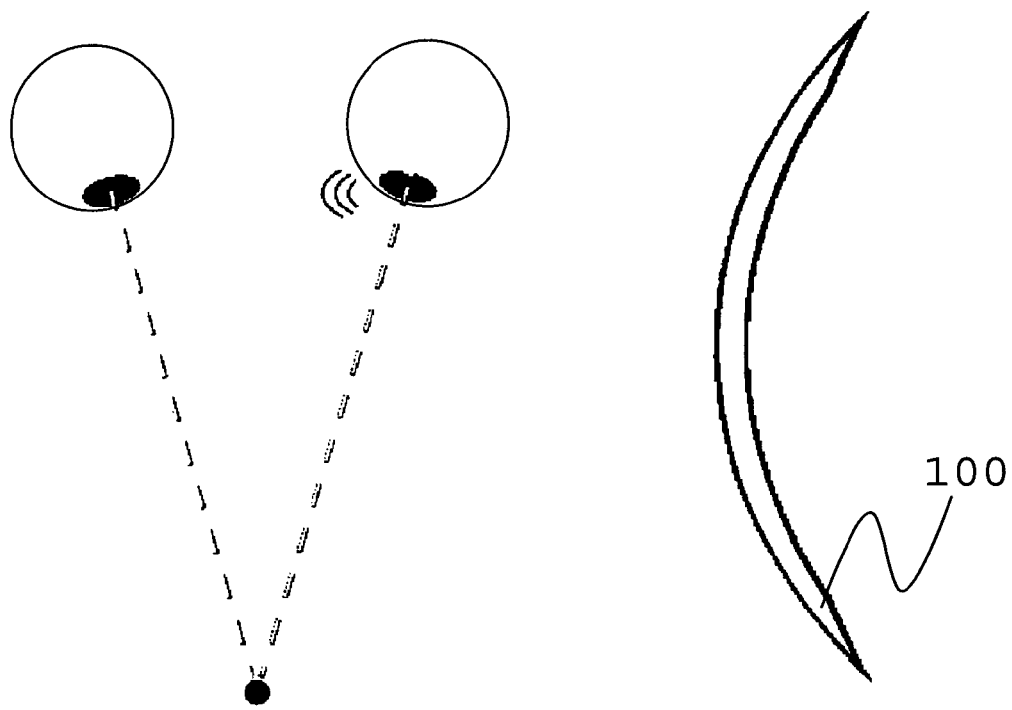
Fig. 9.a
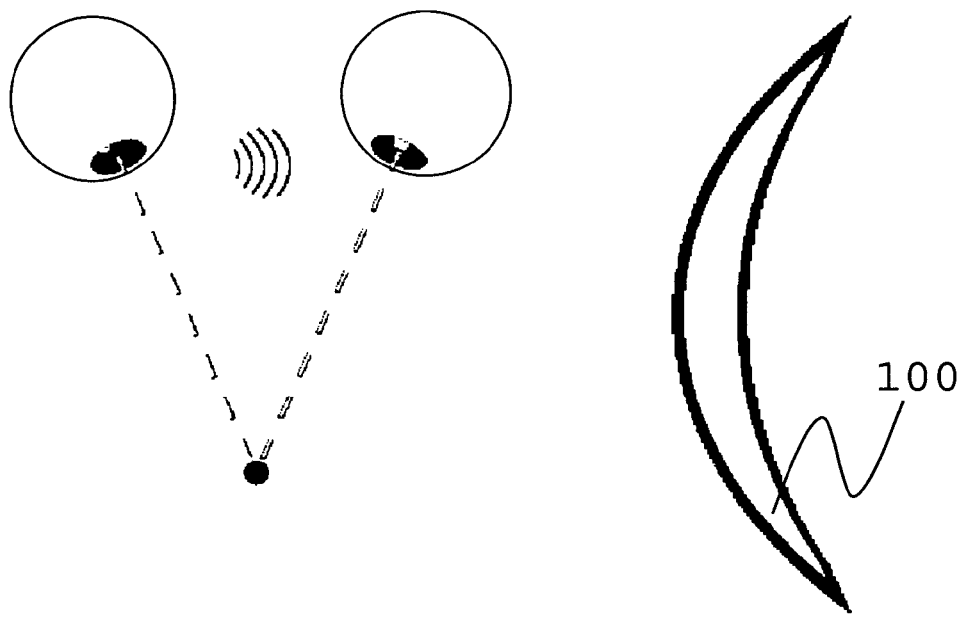
Fig. 9.b

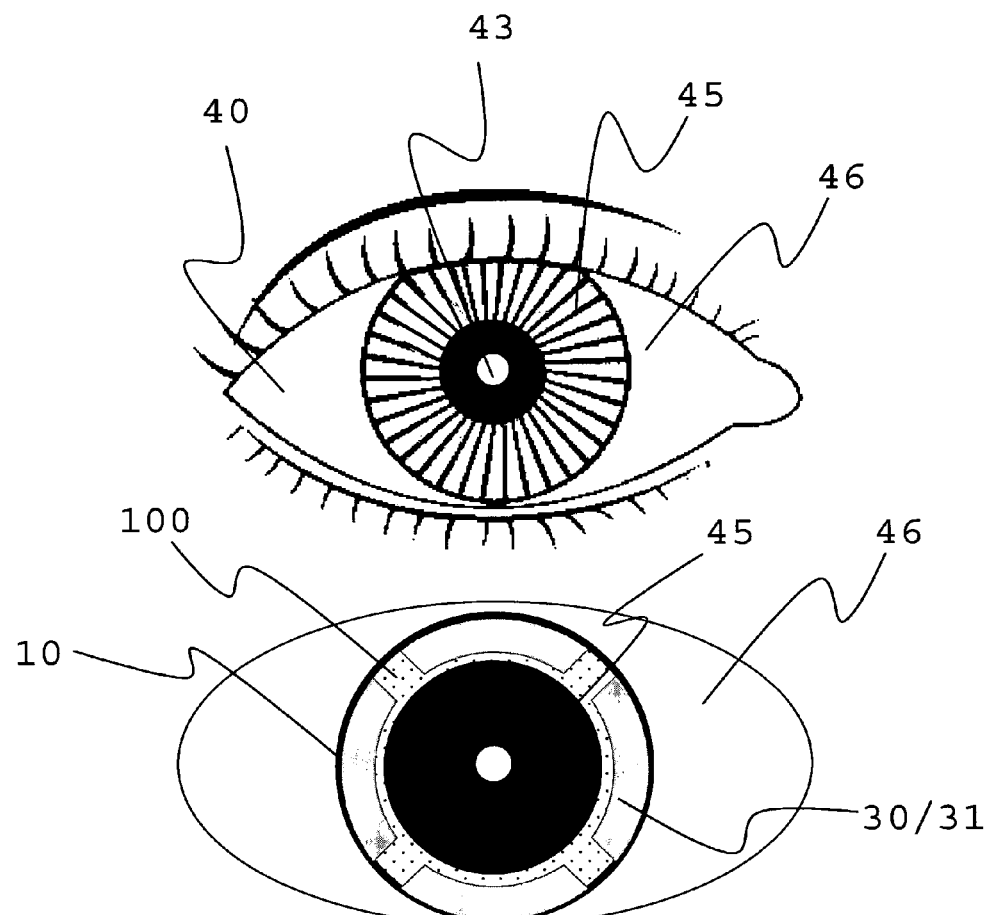
Fig. 10.a
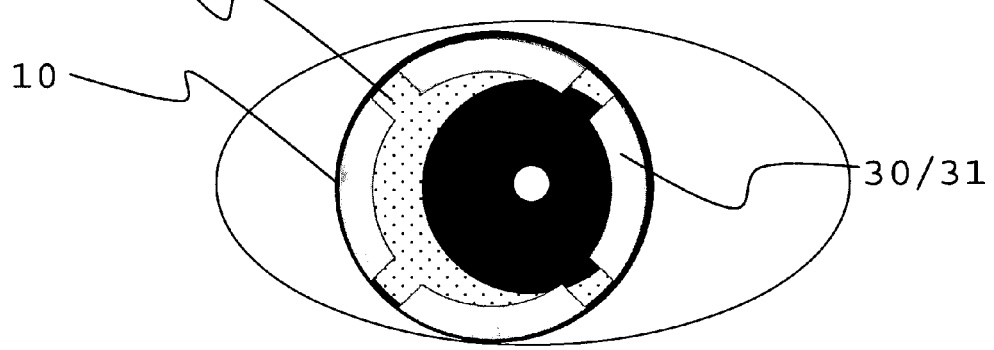
Fig. 10.b

LENS WITH VARIABLE REFRACTION POWER FOR THE HUMAN EYE

CROSS REFERENCE TO RELATED APPLICATIONS

This application is a National Stage of International Application No. PCT/EP2010/002986, filed on May 15, 2010, which claims priority to German Application No. 10 2009 021 699.5 filed May 17, 2009, German Application No. 10 2009 040 933.5 filed Sep. 11, 2009, and U.S. Provisional Application No. 61/284,863 filed Dec. 28, 2009. The content of the prior applications are incorporated herein by reference in their entirety.

DESCRIPTION OF THE INVENTION

The present invention concerns a visual aid for the eye for reinstating eye-accommodability, a process for the reinstatement of the eye-accommodability as well as a process for production of such a visual aid.

BACKGROUND OF THE INVENTION

In the human eye, the lens is embedded behind pupil and iris within a notch or recess of the vitreous body. The function of the lens is to adapt the eye from close vision to far vision and vice versa. For example, while reading a book, the eye has to be adjusted to a short distance. Contrary, while looking to an object in far distance, the lens has to perform a kind of "switching process".

The lens is kept in its position by means of a kind of "suspension device", the so-called zonules or suspensory ligaments, which emanate from the ciliary body. This ciliary body features the ciliary muscle, which is an annular muscle band. The ciliary muscle effectuates a stronger or weaker flection or curvature of the lens. When the ciliary muscle contracts, the zonules relax, such that the flection of the lens increases. Hence, the lens can become rounder with increasing contraction of the ciliary muscle, which increases the refraction power of the lens. This process is called "accommodation". Contrary, when the ciliary muscle relaxes, the lens is straightened by the tension of the zonules.

Incident light rays are refracted variably by different bending states of the lens. The refractive power of the lens is changed. A larger flection of the lens results in a higher refraction of the light rays and a focusing for close vision is achieved. To adapt the lens for far vision, the process proceeds inversely. By alternating its refraction power, the lens enables close vision as well as far vision. The process of accommodation proceeds sort of "automatically", since the ciliary muscle cannot be influenced deliberately.

The natural eye lens of the human starts loosing its elasticity approximately at the age of 40. The lens is not any more able to bend itself so strongly and it looses the aptitude to automatically focus on different distances (accommodation). For example, a 30 years old person is able to focus on a distance of 12 centimeters. In contrast to that, with an age of 40 focusing is possible on a distance of 20 centimeters and with an age of 50 on a distance of 60 centimeters. The loss of accommodability is also known as presbyopia.

The use of reading glasses is one possibility, to enable focusing on close distances. For example, a 60 years old person needs a correction of approximately plus three diopters for being able to focus on a 30 centimeters distance. For focusing on far distance, the glasses have to be removed.

Beyond that, so called bifocal glasses exist, the upper half of which is adapted for far vision and the lower half of which is adapted for close vision. However, the jump or break of vision in the middle of the glasses turns out to be distracting. In so called multifocal glasses these two zones merge continuously. However, also multifocal glasses turn out to be unsuitable for many spectacle wearers. Furthermore, contact lenses are known, which act like a multifocal glass on the eye. However, these lenses have the same drawbacks as the multifocal glasses.

Additionally, multifocal lenses are known, which are implanted as intraocular lenses replacing the natural eye lens. After removal of the body's own lens, intraocular lenses are inserted as implant into the empty capsular bag. The implant is an artificial lens consisting of several annuli with different refraction powers. The implant induces two focal points within the eye, one for far vision and one for close vision. On the distance in between, the patient's focus is not perfect.

Moreover, accommodating intraocular lenses are known. These potentially accommodating lenses concern lenses or lens systems, which are inserted instead of the natural lens after operative removal of the natural lens and which are mostly fixed within the capsular bag. Via a still existing, however, weak residual contractibility of the ciliary muscle and by means of a haptic an axial shift of the lens and thus, a shift of the focal point should be achieved.

The document DE 10 139 027 A1 describes an intraocular lens with preferably four radially outwards extending haptics. The haptics are connected articulately with the optic. By contraction of the ciliary muscle the lens is axially shifted forwards within the optical path by a deflector mechanism and thereby, the refraction power of the whole system is increased. Such implants allow for the reinstatement of an accommodation of approximately 1 dpt to 2 dpt.

This, however, is not sufficient, since for example for the ability to read, an accommodation of higher than 3 dpt has to be realized. Additionally, an exact positioning of the intraocular lens is difficult.

DESCRIPTION OF THE INVENTION

Based on this background information, the object of the present invention is to provide a visual aid, which at least diminishes the above-described drawbacks of the state of the art.

The refraction power of the visual aid should be continuously adaptable to the necessary accommodation requirements.

The visual aid should be suitable for everyday use.

Furthermore, the visual aid should be economically producible.

These problems are solved by the lens, the optical system, and the process for accommodation as well as the production process according to the independent claims. Advantageous embodiments are subject of the respective dependent claims.

The present invention bases on the fact that accommodation requirement and motor function of the eye, i.e. the movement of the eyes, are closely interrelated. In detail, accommodation of the eye lenses and the convergence movement of the eyes or the pupils are closely connected to one another.

The general idea of the invention bases on the concept to determine the accommodation requirement from the position of the eyes to one another or from the orientation of the eyes to one another and to provide the necessary accommodation for the eyes by a visual aid, especially without encroaching on the motor function of the eyes.

The first embodiment of the present application claims a lens, especially with variable refraction power, comprising the following components:

means for adaptation of the refraction power, especially by a shift of the lens curvature, as reaction to a control signal, at least one position locator, means for detection of a relative position of the position locator with respect to at least another position locator which is arranged on another lens, in particular such that an eye orientation is determinable or determined from the detected relative position of the position locator with respect to the other position locator, means for generation of a control signal in order to adapt the refraction power of the lens to the detected relative position, in particular such that a required refraction power or accommodation for the determined eye orientation is provided or can be provided, and at least one device for power supply of at least one part of the components of the lens.

All components of the lens according to the invention are arranged on the lens. Hence, a compact optical system is provided, which is easy to handle.

The lens is preferably an accommodating lens. The means for detection of the relative position of the position locator with respect to the other position locator can comprise the first position locator.

A process for production of the lens is also within the scope of the invention, the lens being constructed as an intraocular lens or as a contact lens, wherein the process comprises arranging of the following components on the lens:

means for adaptation of the refraction power of the lens, at least one position locator for detection of a relative position of the position locator with respect to a reference point, especially means for generation of a control signal in order to adapt the refraction power to a the distinct relative position, and especially at least one device for power supply of at least one part of the components of the lens.

Said reference point preferably is provided by a position locator which is arranged on another lens, so that no external reference point is necessary.

The present application additionally claims an optical system as a visual aid, especially with variable refraction power, comprising a first lens for positioning on or in a first eye and a second lens for positioning on or in a second eye, comprising the following components:

first means which are arranged on the first lens, the first means being adapted to change the refraction power of the first lens, especially via a change of the lens curvature, as reaction to a first control signal, and second means which are arranged on the second lens, the second means being adapted to change the refraction power of the second lens, especially via a change of the lens curvature, as a reaction to a second control signal, means for detection of a relative position or orientation of the first eye with respect to the second eye, comprising at least one first position locator which is arranged on the first lens, and at least one second position locator which is arranged on the second lens, in particular wherein a relative position of the first position locator with respect to the second position locator is detectable or detected, such that the orientation of the first eye with respect to the second eye is determinable or determined, means for generation of the first and second control signals in order to adapt the refraction power of the first and the second lens to the detected relative position, in particular such that a required refraction power or accommodation for the determined orientation of the first eye with respect to the second eye is provided or can be provided, at least one first device for power supply, which is especially arranged on the first lens, and/or at least one second device for power supply of at least parts of the components of the first and/or second lens, which is especially arranged on the second lens. The above mentioned optical system as a visual aid also can be named visual aid only.

Also a process for adaptation of the refraction power is within the scope of the invention. The process for adaptation of the refraction power especially comprises the accommodation of a first lens within a first eye and of a second lens within a second eye, wherein the first lens and the second lens each are embodied as intraocular lens or as contact lens, the process comprising the steps:

detecting a relative position of the first eye with respect to the second eye, generating a first control signal and/or a second control signal in order to adapt the refraction power of the first lens and of the second lens to the detected relative position, adapting the refraction power of the first lens and the refraction power of the second lens as reaction to the first and/or second control signal.

When the first lens and the second lens are adapted for the first time to the spectacle wearer's individual properties, the process for adaptation of the refraction power is a calibration process of the first lens and the second lens. The position of the eyes to one another, especially the distance of the eyes to one another and/or the included angle, is measured. At least a position of the eyes for the distance vision (looking straight ahead) and a position of the eyes for close-up vision are measured. The measured positions of the eyes are related each to the necessary refraction power.

The vision aid is preferably an accommodating vision aid. The vision aid can also be called an optical system. The means for detection of the relative position are preferably arranged entirely on the first and/or on the second lens. Preferably, also the means for generation of the first control signal and the means for generation of the second control signal are arranged on the first and/or on the second lens. Preferably, the first device for power supply is arranged on the first lens and/or the second device for power supply is arranged on the second lens. Preferably all components are arranged or positioned on the first lens and/or the second lens.

The production process is especially appropriate for the production of a lens and of a first and a second lens, respectively, all lenses exhibiting the features according to the invention. The process for accommodation is especially appropriate for its execution by means of the lens and/or the optical system according to the invention. The lens and/or the optical system is or are especially appropriate for execution of the process of accommodation according to the invention.

The embodiments described in the following are only displayed with respect to said lens. The embodiments, however, also display embodiments of the above-described first lens and the above-described second lens with first and second components, respectively and of the above described other lens with other components.

In one embodiment of the invention, the lens is embodied as intraocular lens, i.e. as an implant. In another embodiment of the invention, the lens is embodied as a contact lens. Therefore, the lens according to the invention is a lens for inserting into an eye or positioning or placing in or on an eye.

The above-mentioned means for detection of the relative position and the means for generation of the control signal can be provided by a single device. Furthermore, said means for detection of the relative position themselves can be the position locator for the other position locator. According to this embodiment, the means for detection of the relative position and the position locator are a single device. The means for detection of the relative position preferably can also be arranged, especially entirely or partly, outside of the lens, wherein the arrangement is preferably stationary. The means can be arranged outside of the body, e.g. as part of glasses, or inside the body, e.g. embedded into a bone. The means can also be provided within a kind of band-aid or adhesive tape. The adhesive tape is preferably transparent or of skin color and is affixed to the skin. The strip or adhesive tape is for example affixed at the same time when the lenses are positioned or inserted. By way of this fastening, another position locator or reference point can easily be arranged or provided on the skin. With the aid of a third reference point or at least another reference point, the detection of the relative position of the position locators to one another can also be effected indirectly, e.g. by dint of triangulation.

The single components of the lens can be arranged on the upper side of the lens and/or on the lower side of the lens and/or the components can be embedded within or inside of the lens. According to a preferred embodiment of the invention all components are preferably entirely embedded within the material of the lens. For that purpose, known materials, which are already accredited as being compatible, can be used. Elaborate and costly investigations concerning the compatibility of each of the components can be dispensed with.

Preferably, all components are transparent with respect to the optically visible wavelength region or the visible spectrum, such that the appearance of the eye through the lens, especially when designed or embodied as a contact lens, is essentially not changed.

An accommodating visual aid or an accommodating lens comprises or represents an artificial lens, which flexes itself in the same way as its natural counterpart, i.e. which bends itself when the wearer intends to identify something in short distance. By way of the changed curvature of the lens incident light rays are refracted more strongly. The refraction power of the lens is enhanced.

Therefore, means for adaptation of the refraction power according to a first embodiment are embodied as means for adaptation of the refraction power via a change of the lens curvature. The means for the change of the refraction power are means for the change of the curvature of the lens. By dint of the influence of outer forces, the lens or the geometry of the lens is deformed such that the curvature of its light-refracting surface is changed. The optical imaging properties of the lens are influenced or controlled. The means for adaptation of the refraction power are a kind of an actor transferring the control signals into mechanical movement. This embodiment is especially advantageous if the lens is embodied as an intraocular lens, because the exact insertion and positioning of an intraocular lens within the capsular bag of the human eye proves to be extremely difficult. The invention allows adapting or adjusting of the refraction power of the lens to the achieved or final position of the lens within the capsular bag.

According to a preferred embodiment, the means for adaptation of the refraction power comprise a ligature connected to the lens, the ligature being able, especially as a reaction to the control signal, to change or adjust its length. According to one embodiment, the ligature extends at least partly over the circumference or periphery of the lens. The ligature consists of an annulus. This annulus can be a continuous annulus, which extends completely over the circumference of the lens. The annulus, however, can also be a segmented annulus, which extends only in sections over the circumference of the lens. By way of a change of the annulus' length or the annulus' perimeter radial forces are transferred to the lens, which results in a changed curvature of the light refracting surface.

Preferably, means for adaptation of the refraction power, especially the ligature, are embodied as a contracting element. The means for adaptation of the refraction power comprise or the contracting element comprises at least a material selected from the group consisting of an electro-active polymer, a piezo-electric material, a magnetostricitve material, an electrostrictive material and a bimetallic material. The contracting element can also be formed completely from one of these materials or from combinations of these materials.

An electro-active polymer (EAP) is a chemical actor. The EAP exhibits a volume change, especially as a result of an electrically triggered oxidation or reduction. A voltage application provokes a deformation of the piezo-electric material. The magnetostrictive material changes its geometrical dimensions due to the influence of a magnetic field. An electro-strictive material is elastically deformed due to the application of an electrical field. The curvature of a body that is formed from a bimetallic material can be controlled by temperature changes. This temperature change can for example be effectuated by a current flow.

A first alternative or complementary variant for the change of the lens' curvature represents the electrowetting. A second alternative or complementary variant for the change of the lens' curvature represents the geometrical change by way of a pressure change within a fluid-filled chamber. This pressure change occurs for example with respect to the ambient pressure.

Furthermore, the means for adaptation of the refraction power according to a second embodiment are embodied to a change of the refractive index of the lens. The change of the refractive index is preferably achieved essentially without changing the curvature of the lens. According to a possible variant, so-called electro-optical materials effect this change. The refractive index of such electro-optical materials can be influenced for example by an electric field, by a magnetic field and/or by an electromagnetic field. A defined refractive index distribution within the lens can thus be adjusted. The electro-optical material can be provided for example as electro-optical polymer. Changing the density of a compressive fluid provides another possibility for the change of the refractive index.

The adaptation of the refraction power results as a reaction to the control signal. The control signal comprises information concerning the necessary refraction power, as for example the lens curvature. The control signal, in a manner of speaking, represents a kind of a actuating or regulating signal. The means for generation of the control signal are or comprise for example a device for generating a voltage. According to this embodiment, the control signal is for example a voltage signal, which is proportional to the refraction power. The first control signal and the second control signal can also be provided as one single control signal.

The device for power supply is connected to all or only to parts of the components, depending on the precise embodiment of the components. Preferably, all components, which require electric energy for their operation, are connected to the device for power supply.

According to one embodiment of the invention, the device for power supply comprises an accumulator and/or a battery. As an alternative or a complementary to the accumulator and/or the battery the device for power supply comprises at least one photovoltaic element or device. According to another alternative or complementary embodiment the device for power supply comprises at least one thermo-electric element or device.

If for example a battery is provided for power supply, a safe operation can be assured, which is independent of outside influences as e.g., the light incidence. Since batteries cannot be recharged, the battery has to be replaced when empty or the lens has to be disposed of. Such an embodiment is for example interesting if the contact lenses are used as so-called monthly contact lenses.

The photovoltaic element, which can generally also be called solar cell, can allow for recharging of an accumulator and/or provide a direct power supply for at least parts of the components, depending on the embodiment of the invention. Thus, a long time or a permanent operation of the lens can be assured.

The embodiment with an accumulator and/or a battery can furthermore comprise means for, especially the initial, activation of the accumulator and/or the battery. According to another embodiment, an indicator for the accumulator and/or battery charge condition can be provided on the lens.

The device for power supply, especially the photovoltaic element, extends at least in sections over the circumference or periphery of the lens. Preferably, the device for power supply, especially the photovoltaic element, is formed as an annulus. The annulus can be an annulus, which extends completely over the circumference of the lens. The annulus can also be a segmented annulus, which extends only in sections over the circumference of the lens. According to a variant of the invention, essentially the whole area or surface of the lens is formed as the photovoltaic element. Thus, a large-area collection of incident radiant power can be accomplished. The properties described for the photovoltaic element also apply to the thermo-electrical element.

According to an alternative or complementary embodiment of the invention, the device for power supply is arranged outside of the lens. The power supply is achieved by wireless energy transport. The power supply is carried out by inductive coupling or electro-magnetic induction.

The necessary refraction power, especially the necessary curvature is determined from the detected relative position of the eyes to one another. The relative position can be determined from the distance of the eyes or of the pupils to one another and/or from the angle, the so-called convergence angle, which is formed between the eyes. Subsequently, the refraction power is controlled. The detection of the relative position of the eyes is achieved by the detection of the relative position of the position locator with respect to the other position locator or by determining the relative position of the first position locator with respect to the second position locator. In particular no external reference point is necessary. The position locator also can be called position sensor.

In general, accommodation concerns both eyes to the same extent, although the refraction of both eyes can be different. The wearers of the lenses in general feature differently positioned eyes. Therefore, it is necessary that an optician or an ophthalmologist performs the initial adaptation of the lenses to the wearer's individual properties. The initial adaptation of the lenses is accomplished for example in the inserted state, for example when the contact lenses are positioned on the eyes.

The position of the eyes to one another, especially the distance between the eyes and/or the included angle is determined or detected and the determined values are related to the necessary refraction power. Hence, the optical system is calibrated, especially with reference to the position of the eyes to one another and/or the position of the respective inserted lens on or within the eye.

According to a first embodiment, the detected relation can directly be related to the control signal to be generated for adaptation of the refraction power of the lens. This relation can be stored in a kind of table or memory device. The table or the memory device can be part of the means for detection of the relative position and/or the means for generation of the control signal. Hence, a detected relative position can be directly transformed into a control signal. According to a second embodiment, in contrast, means for determining the refraction power of the lens, especially the lens curvature, in relation to the determined relative position are provided, i.e. the control signal has yet to be calculated.

The detection of the relative position of the eyes is effected by the position of the position locator with respect to the other position locator. This, however, implies that the position of the respective lens on or within the eye is "fixed". In deed, contact lenses are floatingly supported by dint of a precorneal film such that the contact lenses are movable on the eye. In order to reliably detect the position of the contact lens relative to the eye, for example to the pupil, especially to the pupil center and/or the cornea, means for detection of the relative position of the contact lens with respect to an eye on which the contact lens is position in inserted state are provided.

Additionally, the position of an intraocular lens within the eye can change, such that an adjustment or a readjustment is required. In order to reliably detect the position of the intraocular lens relatively to the eye, for example to the pupil, especially to the pupil center, according to an embodiment of the invention, means for detection of the relative position of the lens to one eye in which the intraocular lens is positioned in inserted state are provided. Preferably, the pupillary reflex is considered. The aperture or the diameter of the pupil becomes smaller in accommodated state (short focus reaction).

Preferably, the means for detection of the relative position of the position locator with respect to the other position locator are additionally designed to detect the relative position of the lens with respect to the eye. According to a preferred version of the invention, these means are coupled to the photovoltaic element such that an electrical power, which is provided by the photovoltaic element, can be analyzed and such that the relative position can be deduced from a changed electrical power. For that purpose, the photovoltaic element preferably has a segmented form. Furthermore, the photovoltaic element is preferably arranged closer to the center of the lens, preferably the contact lens, than the means for adaptation of the refraction power. For further details concerning this embodiment, reference is made to FIGS. 9.a and 9.b.

According to an embodiment, the means for detection of the relative position of the position locator with reference to the other position locator or the means for detection of the relative position of the first eye with respect to the second eye are designed for distance measurement and/or angular measurement. Preferably, the means are designed for inductive and/or capacitive distance measurement and/or for distance measurement via a signal propagation delay measurement and/or for distance measurement via an interference measurement. According to a first variant of the invention, the position locator comprises a metallic device. According to a second variant of the invention, the position locator comprises a coil or the position locator is embodied as a coil. According to a third variant, the position locator is a chip, for example a RFID-chip (Radio Frequency Identification). According to a fourth variant, the position locator is designed as a sender and/or receiver of preferably electromagnetic radiation or waves, for example radio waves.

In order to reliably detect a change in the position or a rotation, for example of the contact lens floating on the pre-corneal film and with respect to the eye, according to a further embodiment of the invention, a multitude of position locators is arranged over the circumference or periphery of the lens. This is for example relevant, if the position locators are not transparent with respect to the visible spectrum or the visible optical wavelength range. However, if it is possible to design a transparent position locator, it is sufficient to arrange one single position locator, for example in the center of the lens.

According to a preferred embodiment of the invention, the means for detection of the relative position of the position locators and/or of the eyes comprise a system for information processing. The system for information processing is especially designed as chip or microchip.

The position locator, the means for detection of the relative position of the position locators or of the eyes, the means for generation of the control signal and/or the means for detection of the relative position of the lens with respect to the eye can for example be integrated in one single chip.

The accommodation requirement is, additionally to the convergence movement of the eyes, also connected to the pupillary reflex of the eyes. As already discussed above, the pupil's diameter becomes smaller in the accommodated state. Thus, additionally or alternately to the above-described position detection of the eyes, the pupillary reflex can be considered as one or as another parameter for determination of the necessary refraction power. For that purpose, an electric power supplied by a photovoltaic element can be analyzed. The necessary accommodation can be deduced from a changed electric power. This embodiment is especially suitable for an intraocular lens.

As an alternative or a complement, especially for detection of the pupillary reflex, also the light reflected by the retina can be considered. For that purpose, at least one photovoltaic element is arranged on the lens, the photovoltaic element being assigned to the light, which is reflected by the retina. For that purpose, the assigned photovoltaic element is arranged for example on the backside of the lens, especially of an intraocular lens.

The lens according to the invention is especially suitable for the human and/or an animal eye. If only one eye does not possess the ability to accommodate anymore, it is sufficient to use the lens according to the invention only for the eye, which does not accommodate anymore. For the still accommodating eye, a contact lens would suffice which solely comprises the position locator in order to be able to detect the relative position of the eyes. Thus, the invention comprises a preferably accommodating visual aid, which comprises at least one lens according to the present invention.

The present invention will be explained in detail by the following embodiments. For that purpose, reference is made to the drawings. The same reference numerals within single figures refer to identical or similar features.

FIGS. 1.*a* and 1.*b* schematically show exemplary a first embodiment of the lens according to the invention in a top view and a sectional view.

FIGS. 2.*a* and 2.*b* schematically display exemplary a second embodiment of the lens according to the invention in a top view and a sectional view.

FIGS. 3.*a* and 3.*b* schematically show exemplary a third embodiment of the lens according to the invention in a top view and in a sectional view.

FIGS. 4.*a* and 4.*b* schematically depict exemplary a forth embodiment of the lens according to the invention in a top view and in a sectional view.

FIGS. 5.*a* and 5.*b* schematically display exemplary a fifth embodiment of the lens according to the invention in a top view and in a sectional view.

FIGS. 6.*a* and 6.*b* schematically show the position of a pair of eyes for different distances as well as the changed curvature of the inserted contact lens in its basic state and in its contracted (accommodated) state in sectional views.

FIGS. 7.*a* and 7.*b* illustrate the contact lens from FIGS. 6.*a* and 6.*b* in magnification.

FIGS. 8.*a* and 8.*b* illustrate the arrangement of the contact lenses displayed in the FIGS. 6.*a* and 6.*b* on the eye in a front view.

FIGS. 9.*a* and 9.*b* schematically show the position of a pair of eyes for different distances and the respective curvature of an inserted contact lens in the basic state and in contracted (accommodated) state.

FIGS. 10.*a* and 10.*b* illustrate the detection of the position of the contact lens with respect to the eye on which it is positioned in inserted state.

DETAILED DESCRIPTION OF THE INVENTION

The following description of the figures refers solely to a lens 100 according to the invention. This lens 100 represents the first lens mentioned in the general part of the description as well as the second lens comprising respective first and second components.

In order to simplify the description, electrical connections between single components, e.g. between a photovoltaic element 31 and a means for adaptation of the refraction power 10, are not shown in any of the figures. Electrical connections can be formed by a transparent, electroconductive material. In following, the illustration of the single features of a lens 100 according to the invention is effected exclusively on a contact lens 100 by way of example.

The contact lens 100 can be produced from a material commonly used for contact lenses. A rigid contact lens can for example be produced from polymethyl methacrylate. Soft contact lenses can for example be produced from hydroxyethyl methacrylate and/or silicon rubber. For that purpose, the components of the invention can be integrated or installed in simple manner into already known "lens systems".

Furthermore, the means for detection of the relevant position of the position locator 20 with respect to the other position locator as well as means for generation of the control signal are not shown in the figures. These means can be provided by a system for information processing as e.g., a chip or a microchip.

Within the figures, the means for adaptation of the refraction power 10 in each case is illustrated as contracting device 10. In detail, the contracting device 10, which is also called contractile element, is formed as contracting ligature 10. One advantage of such a contracting ligature is especially based on the low energy requirement for contraction, since only circularly acting powers have to be activated. It should, however, be noted that each means, which achieves a change in the refraction power and which is appropriate for the invention, can be used.

According to one embodiment, the contracting ligature 10 is provided by an electro-active polymer (EAP). The EAP is an electroconductive polymer, which exhibits a certain molecular structure. The EAP shows for example a volume reduction in case of an electrically induced oxidation or reduction. When the EAP is formed as a layer on a flexible substrate and connected to the substrate, the formed "sandwich" flexes due to the volume reduction similar to a bimetal spring. When the EAP extends as a ligature 10 over the circumference of the contact lens 100, according to the invention, volume changes of the ligature material result in a length change of the ligature 10 and thus in a lens deformation.

In FIGS. 1.a and 1.b a first embodiment of a contact lens 100 according to the invention is illustrated. FIG. 1.a shows a view on the topside or surface of the contact lens 100. FIG. 1.b shows a sectional view of the contact lanes 100 along the axis A-A. Devices for power supply 30, means for adaptation of the refraction power 10, and a multitude of position locators 20, for example four position locators, are arranged on the contact lens 100.

The device for power supply as shown in FIGS. 1.a and 1.b is formed as photovoltaic element 31. It is configured as an annulus, which extends continuously over the circumference of the contact lens 100. The photovoltaic element 31 preferably is applied on the contact lens 100 such, that it is arranged directly adjacent to the cornea in inserted state. The photovoltaic element 31 can be based on organic solar cells. One example for organic solar cells are polymer-fullerene solar cells. On the one hand, these are flexible. On the other hand, they can be produced by printing at room temperature.

As already described above, the means for adaptation of the refraction power 10 is formed as contracting ligature 10. The ligature 10 is formed as an annulus, which continuously extends over the circumference of the contact lens 100. With respect to the photovoltaic element 31, the ligature 10 is arranged further outside, in direction to the edge of the contact lens 100. The ligature 10 can also be arranged on the outermost edge of the contact lens 100 or directly on the edge of the contact lens 100.

For detection of the eye position or the position of the eyes relatively to one another, four position locators 20 are arranged on the contact lens. The position locators 20 are distributed over the circumference of the contact lens 100. A multitude of position locators 20 ensures that the distance of the eyes can be reliably detected even if the contact lens 100 rotates on the eye.

The eye position can be determined or detected by measuring the eye's distance and/or by measuring the convergence angle β, which is enclosed between both eyes or between the pupils. Further details concerning this matter are disclosed with respect to the FIGS. 6.a to 8.b. In the following, two possible measurement methods are briefly described.

The distance measurement can for example be carried out "capacitively". Capacitive distance sensors require two metallic parts, which are isolated from each other. The distance is determined by the capacity existing between the two parts. A first position locator 20 on the first contact lens 100 provides a first metallic part. A second position locator 20 on a second contact lens 100 provides a second metallic part. The second position locator 20 being a so-called sensor electrode is for example integrated into an oscillating circuit, the frequency of which increases with increasing distance. According to this embodiment, the first position locators 20 of the first contact lens 100 and the second position locators 20 of the second contact lens thus together form a distance sensor. The detected frequencies are sent to an evaluation unit. This evaluation unit is for example part of the means for detection of the relative position of the position locators.

The distance measurement and/or the angular measurement can also be carried out "inductively". In such an embodiment the position locators 20 are formed as coils. An alternating magnetic field is generated. Within the coil a voltage is induced. From induced voltages the three-dimensional orientation of the eyes can be deduced. Induced voltages are measured and supplied to an evaluation unit.

The distance measurement and/or the angular measurement can also be carried out by a signal propagation time measurement and/or an interference measurement. For further details, reference is made to the description of FIGS. 9.a and 9.b.

In FIGS. 2.a to 5.b further embodiments of the contact lens 100 according to the invention are shown. In order to prevent repetitions, reference is made to the description of FIGS. 1.a and 1.b for identical components.

FIGS. 2.a and 2.b show an embodiment of the contact lens 100 according to the invention, in which energy storing devices 32 as for example batteries instead of the photovoltaic elements 31 are provided. Thus, an operation of the contact lenses 100 independently of incident light is possible. Additionally, a reliable operation of the contact lenses 100 in darkness is ensured.

FIGS. 3.a and 3.b show a combination of the embodiments according to the invention of FIGS. 1.a to 2.b. The energy storing devices 32 and the photovoltaic elements 31 are arranged on the contact lens 100. The energy storing devices 32 and the photovoltaic elements 32 are connected such that the energy storing devices 32 are charged by the electric energy produced by the photovoltaic elements 31.

The single components are arranged preferably outside of the contact lens' center and hence, outside of the area which is relevant for the optical imaging properties of the contact lens 100 (see FIGS. 1.a to 3.b). If the components are formed such that they do not negatively influence the imaging properties, a restriction to the area outside of the lens' center is not compelling.

With respect to the above, a first embodiment is schematically shown in FIGS. 4.a and 4.b. A photovoltaic element 31, which is transparent with respect to the visible spectrum, however, active with respect to for example the infra red and/or the ultra violet spectrum is arranged on the whole area or essentially the whole area of the contact lens 100. Due to the augmented area of this embodiment an enhanced energy yield can be achieved. As an additional embodiment, the contracting ligature 10 is not anymore formed continuously over the circumference of the lens 100. The contracting ligature is segmented and thus non-continuously formed over the circumference. Furthermore, by example only three position locators 20 are arranged on the lens 100.

As a further example, a position locator 20, which is transparent with respect to the relevant visible spectrum, is arranged in the center of the contact lens 100 as shown in FIGS. 5.a and 5.b. According to this embodiment, one position locator 20 per lens 100 is sufficient in order to detect the position of the contact lenses 100 to one another. This is because a rotation of the lens 100 does not influence the distance of the position locators 20 anymore. As an additional embodiment, the photovoltaic element 31 is not anymore formed continuously over the circumference of the contact lens 100. The photovoltaic element 31 is segmented and thus not formed continuously over the circumference. The segmented embodiment is especially advantageous, if further to the position of the eyes to one another also the position of the lens with respect to the eye should be detected. This embodiment is illustrated in detail in FIGS. 10.a and 10.b.

The principle of the "coupling" of accommodation requirement and the eyes' positions is once again illustrated in FIGS. 6.a to 8.b. FIGS. 6.a and 6.b illustrate the position of a pair of eyes for different distances and the changed curvature of an inserted contact lens, firstly in its basic state (FIG. 6.a, right side) and secondly in its contracted (accommodated) state (FIG. 6.b, right side). The three-dimensional relation of a person's eyes changes if the person looks at objects in different distances. If the object that the person looks at is situated close to this person, the eyes and especially the pupils are positioned closer to one another than if the person looks at an object that is situated further away (see FIGS. 6.a and 6.b, left side each).

Further to the distance measurement, the measurement of the convergence angle β can alternatively or supplementary be carried out. The convergence angle β describes the angle that is enclosed by both eyes. The refraction power is then adapted in dependence on the convergence angle β detected as described above.

According to the present embodiment, the refraction power is adjusted by an adjustment of the length of the ligature 10 (see FIGS. 6.a and 6.b, right side each). FIGS. 7.a and 7.b show the contact lens 100 from FIGS. 6.a (right side) and 6.b (right side) in an augmented detailed view. The contact lens is illustrated in a simplified form with only the contracting ligature 10. FIG. 7.a shows the positioned contact lens 100 in its basic state. The basic state represents the "relaxed", i.e. the non-contracted state. FIG. 7.b shows the positioned contact lens 100 in its contracted state (accommodation). The diameter of ligature 10 formed as an annulus is reduced from diameter d1 in the basic state to diameter d2 in the contracted state. The contraction can, as indicated in FIG. 7.b, result in a slight lift-off of the center of the contact lens 100 from the cornea 45 of the eye 40, however, without causing a complete detachment of the lens 100 from the eye 40.

In the embodiment of an intraocular lens, the contact lens 100 according to the invention shown for instance in FIGS. 7.a and 7.b is replaced by an intraocular lens according to the invention. The ocular lens 41 shown in FIGS. 7.a and 7.b is replaced by said intraocular lens according to the invention. The described features of the contact lens 100 according to the invention can be applied to said intraocular lens according to the invention.

FIGS. 8.a and 8.b illustrate in a front view the respective position of the pair of eyes with inserted contact lenses 100 in their basic state and in their accommodated state, respectively. FIG. 8.a shows the positioned contact lens 100 in its basic state. FIG. 8.b shows the positioned contact lens 100 in its contracted state. The diameter of the ligature 10 formed as annulus is reduced from diameter d1 in the basic state to diameter d2 in the contracted state. The shortening of the length of the contracting ligature 10, which loops the contact lens, results in the desired deformation or vault of the contact lens 100.

The necessary accommodation requirement is determined by the movement of the pair of eyes or by the position of the eyes 40 to one another. The four position locators 20 on the respective contact lens 100, as presented, determine the position of the eyes 40 to one another. By way of example, the distances between two position locators 20 are given. In the non-contracted state, these position locators 20 possess the distances A1 and A2. In the accommodated state, the distances shorten to a1 or a2, respectively. For a more precise measurement of the relative eyes' position, preferably the respective distances of all position locators 20 to each other should be considered.

FIGS. 9.a and 9.b schematically show the position of a pair of eyes for different distances and the respectively changed curvature of the inserted contact lenses in their basic state (FIG. 9.a) and in their accommodated state (FIG. 9.b). The distance measurement and/or the angular measurement is or are illustrated as a propagation time measurement of the signals and as a interference measurement, by way of example. Especially the position locators 20 are configured each as sender and/or receiver of waves, preferably of radio waves. The waves can be provided as puls and/or as modulated waves. Preferably, sender and receiver are synchronized.

The distance of the two position locators or the relative distance of the two lenses to one another is determined by a propagation time measurement from a first position locator arranged on a first lens to a second position locator arranged on a second lens.

The distance measurement and/or the angular measurement according to the interference measurement, is carried out by the measurement of a changed intensity. Interference describes the superposition of two or more wave trains with sufficient coherence at the same point in space, for example in a detector arranged in a receiver. The superposition of the wave trains results in an intensity distribution, which depends on amplitudes and phase differences. A changed relative position of the lenses 100 thus can be observed as an amplification (interference maximum=constructive superposition), an attenuation or even an erasure (interference minimum=destructive superposition) of the waves. This change can for example be detected by aid of a preferably optical detector and especially by way of a changed voltage. If the wavelength is adapted to the distances that should be measured, the relative distance can be unambiguously determined. This case is realized for a human if the wavelength lies within a range of several millimeters, e.g. of approximately 1 mm to approximately 3 mm.

Finally, FIGS. 10.a and 10.b illustrate the detection of the position of the contact lens 100 with respect to the eye 40 on which it is positioned in inserted state. The figures show top views on one eye 40 with inserted contact lens 100. The contact lens 100 essentially corresponds to the contact lens 100 that is described with respect to FIGS. 5.a and 5.b. As a "characteristic", the contact lens 100 exhibits a segmented photovoltaic element 31.

For the detection of the position of the inserted lens 100 relatively to the eye 40, the light reflected by the eye 40 is used or analyzed. The intensity of the reflected light depends on the optical properties of the eye's surface as reflection face. The white or "light" sclera consisting of connective tissue forms the outermost layer of the eye ball. The sclera changes into the transparent or "dark" cornea 45 in the front part of the eye 40. It can be detected if the respective part of the lens 100 lies on the "dark" cornea 45 of the eye 40 or if the respective part of the lens 100 lies on the "light" sclera 46 and thus showing a higher reflectance.

The photovoltaic element 31 is preferably arranged on the contact lens 100 such that it is neighboring or directly adjacent to the cornea 45 in the inserted state of the contact lens 100. This arrangement is illustrated in FIG. 10.a. In this example, four segments of the photovoltaic element 31 are distributed on the sclera 46 outside the circumference of the dark cornea 45. A maximum of converted electrical energy can be expected, if the lens 100 is arranged as centrically on the eye 40 as shown in FIG. 10.a. This is because the photovoltaic element 31 or its four segments rest completely on or above the light sclera 46. If, however, the contact lens 100 is shifted relatively to the eye 40, at least one segment of the photovoltaic element 31 rests at least partly on the dark cornea 45. This results in a reduced electric power, which is illustrated in FIG. 10.b.

The generated electric power is analyzed. For that purpose, the electric power of each segment and of all segments is determined. The electric power of each segment is then compared with the electric power of all other segments. By considering the electric power per segment, the position of the contact lens 100 relative to the eye 40 can be detected. Due to the segmentation of the photovoltaic element 31 into four separately "converting" devices, position information of the four devices is available. The allocation of the relative electrical powers to the position of the contact lens 100 on the eye 40 can be achieved by aid of a calibration.

For a person skilled in the art it is obvious that the embodiments described should be understood as examples only. The invention is not limited to these examples, but can be varied in manifold forms without leaving the idea of the invention. Features of single embodiments and features described in the general part of the description can be combined in any way.

LIST OF REFERENCE NUMERALS 10 means for adaptation of the refraction power or ligature
20 position locator
30 device for power supply
31 photovoltaic element or solar cell
32 energy storing device or battery or accumulator
40 eye
41 ocular lens
42 zonules
43 pupil
44 iris
45 cornea
46 sclera
100 contact lens

The invention claimed is:

1. A contact lens comprising the following components:
means for adaptation of the refraction power as reaction to a control signal,
at least one position locator,
means for detection of a relative position of the position locator with respect to at least one further position locator being arranged on a further lens,
means for generation of the control signal in order to adapt the refraction power of the lens to the detected relative position, and
at least one device for power supply for at least parts of the components of the lens.

2. The lens as claimed in claim 1, wherein the means for adaptation of the refraction power are embodied as means for adaptation of the refraction power by changing of a curvature of the lens and/or wherein the means for adaptation of the refraction power are embodied to achieve a change of the refractive index of the lens.

3. The lens as claimed in claim 1, wherein the means for adaptation of the refraction power comprise a contracting device preferably wherein the contracting device comprises at least one material selected from the group consisting of an electro-active polymer, a piezo-electric material, a magnetostrictive material, an electrostrictive material and a bimetallic material.

4. The lens as claimed in claim 1, wherein the means for adaptation of the refraction power comprises a ligature, which is connected to the lens and the length of which is changeable preferably wherein the ligature extends at least partly over the circumference of the lens.

5. The lens as claimed in claim 1, wherein the device for power supply comprises an accumulator and/or a batter and/or wherein the device for power supply comprises at least one photovoltaic element and/or a thermoelectric element.

6. The lens as claimed in claim 5, wherein essentially the entire area of the lens is embodied as a photovoltaic element.

7. The lens as claimed in claim 5, wherein the photovoltaic element is arranged closer to the center of the lens than the means for adaptation of the refraction power.

8. The lens as claimed in claim 5, wherein the means for detection of the relative position of the contact lens with respect to an eye are coupled with the photovoltaic element, such that an electric power, which is supplied by the photovoltaic element can be analyzed.

9. The lens as claimed in claim 8, wherein the relative position of the lens with respect to the eye can be determined by way of the changed electrical power.

10. The lens as claimed in claim 1, wherein the device for power supply extends at least partly over the circumference of the lens.

11. The lens as claimed in claim 1, further comprising means for the calculation of the refraction power based on the detected relative position of the position locator with respect to the further position locator.

12. The lens as claimed in claim 1, further comprising means for detection of the relative position of the lens with respect to an eye on which or in which the lens is positioned while inserted.

13. The lens as claimed in claim 1, wherein the means for detection of the relative position of the position locator with respect to the further position locator are designed for an inductive and/or a capacitive distance measurement and/or for a distance measurement by a signal propagation time measurement and/or for a distance measurement by an interference measurement.

14. The lens as claimed in claim 1, wherein a multitude of position locators are distributed over the circumference of the lens or wherein a single position locator is arranged in the center of the lens and/or wherein the means for detection of the relative position of the position locator with respect to the further position locator comprise a system for information processing.

15. A visual aid with variable refraction power, comprising at least one lens as claimed in claim 1.

16. An optical system as visual aid with a first and a second contact lens for positioning on or in a first and a second eye, respectively, comprising following components:
first means for adaptation of the refraction power of the first lens as reaction to a first control signal, wherein the first means for adaptation of the refraction power are arranged on the first lens, and second means for adaptation of the refraction power of the second lens as reaction to a second control signal, wherein the means for adaptation of the refraction power are arranged on the second lens,
means for detection of a relative position of the first eye with respect to the second eye, comprising at least a first position locator being arranged on the first lens and at least a second position locator being arranged on the second lens,
means for generation of the first control signal and the second control signal for adaptation of the refraction power of the first and second lens, respectively, with respect to the detected relative position,
at least one first device for power supply, preferably being arranged on the first lens, supplying power to at least parts of the components of the first lens and/or to at least parts of the components of the second lens, and/or at least one second device for power supply preferably being arranged on the second lens, supplying power to at least parts of the components of the second lens and/or to at least parts of the components of the first lens.

17. A contact lens comprising the following components:

means for adaptation of the refraction power as reaction to a control signal, at least one position locator, means for detection of a relative position of the position locator with respect to at least one further position locator being arranged on a further lens, means for generation of the control signal in order to adapt the refraction power of the lens to the detected relative position; and at least one device for power supply for at least parts of the components of the lens, said device extending at least partly over the circumference of the lens.

18. A contact lens comprising the following components:

means for adaptation of the refraction power as reaction to a control signal, at least one position locator, means for detection of a relative position of the position locator with respect to at least one further position locator being arranged on a further lens, means for generation of the control signal in order to adapt the refraction power of the lens to the detected relative position, and at least one power supply device for at least parts of the components of the lens, wherein essentially the entire area of the lens is embodied as a photovoltaic element.

19. A contact lens comprising the following components:

means for adaptation of the refraction power as reaction to a control signal, at least one position locator, means for detection of a relative position of the position locator with respect to at least one further position locator being arranged on a further lens, means for generation of the control signal in order to adapt the refraction power of the lens to the detected relative position, at least one device for power supply for at least parts of the components of the lens, said device comprising at least one photovoltaic element that is arranged closer to the center of the lens than the means for adaptation of the refraction power.

20. A contact lens comprising the following component;

means for adaptation of the refraction power as reaction to a control signal, at least one position locator, means for detection of a relative position of the position locator with respect to at least one further position locator being arranged on a further lens, means for generation of the control signal in order to adapt the refraction power of the lens to the detected relative position, and at least one device for power supply for at least parts of the components of the lens, wherein a multitude of position locators is distributed over the circumference of the lens or wherein a single position locator is arranged in the center of the lens and/or wherein the means for detection of the relative position of the position locator with respect to the further position locator comprise a system for information processing.

* * * * *